(12) United States Patent
Karl

(10) Patent No.: US 9,698,802 B2
(45) Date of Patent: Jul. 4, 2017

(54) METHOD FOR AMPLIFYING AN ECHO SIGNAL SUITABLE FOR VEHICLE SURROUNDINGS DETECTION AND DEVICE FOR CARRYING OUT THE METHOD

(75) Inventor: Matthias Karl, Ettlingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 418 days.

(21) Appl. No.: 14/344,117

(22) PCT Filed: Jul. 17, 2012

(86) PCT No.: PCT/EP2012/063945
§ 371 (c)(1),
(2), (4) Date: Oct. 14, 2014

(87) PCT Pub. No.: WO2013/037529
PCT Pub. Date: Mar. 21, 2013

(65) Prior Publication Data
US 2015/0077135 A1  Mar. 19, 2015

(30) Foreign Application Priority Data
Sep. 12, 2011  (DE) .................. 10 2011 082 479

(51) Int. Cl.
*H03M 1/00* (2006.01)
*G01S 15/93* (2006.01)
(Continued)

(52) U.S. Cl.
CPC ............ *H03M 1/001* (2013.01); *G01N 27/00* (2013.01); *G01S 7/529* (2013.01); *G01S 13/931* (2013.01);
(Continued)

(58) Field of Classification Search
CPC ........... G01V 9/00; H02M 5/42; G01N 27/00; G01R 27/04
See application file for complete search history.

(56) References Cited

U.S. PATENT DOCUMENTS 5,817,023 A * 10/1998 Daft .................... G10K 11/346
600/447
5,973,996 A   10/1999 Zhevelev et al.
(Continued)

FOREIGN PATENT DOCUMENTS

AT          355185           3/2006
DE      10 041 094          12/2003
(Continued)

*Primary Examiner* — Jermele M Hollington
*Assistant Examiner* — Alvaro Fortich
(74) *Attorney, Agent, or Firm* — Gerard Messina

(57) ABSTRACT

A method for amplifying an echo signal, in which an analog echo signal suitable for detection of a vehicle's surroundings is amplified by a gain dependent on the transit time of the echo signal, the analog echo signal being amplified by an amplifier having a plurality of outputs, each having a different gain, and a downstream A/D converter having a time-variable reference voltage. In the process, there is a switch between the different outputs of the amplifier at predefined switching points in time, and the reference voltage of the A/D converter varies over time between the switching points in time in such a way that the echo signal is present at the output of the A/D converter with a transit time-dependent total gain having a predefined characteristic.

7 Claims, 3 Drawing Sheets

(51) Int. Cl.
*G01S 7/529* (2006.01)
*G01S 13/93* (2006.01)
*H03M 1/18* (2006.01)
*G01N 27/00* (2006.01)
*G01V 9/00* (2006.01)
*H02M 5/42* (2006.01)

(52) U.S. Cl.
CPC .............. *G01S 15/931* (2013.01); *G01V 9/00* (2013.01); *H02M 5/42* (2013.01); *H03M 1/182* (2013.01); *H03M 1/185* (2013.01)

(56) References Cited

U.S. PATENT DOCUMENTS

| | | | | |
|---|---|---|---|---|
| 7,027,356 | B2* | 4/2006 | Bahr | G01S 7/521 367/87 |
| 7,039,549 | B2* | 5/2006 | Eckel | G01S 7/292 367/99 |
| 7,885,144 | B2* | 2/2011 | Oswal | G01S 7/52033 367/65 |
| 2003/0048698 | A1* | 3/2003 | Barnes | G01S 7/52038 367/181 |
| 2005/0088307 | A1* | 4/2005 | Schaffer | G01F 23/284 340/612 |
| 2005/0146433 | A1* | 7/2005 | Waltermann | G01S 15/74 340/553 |
| 2005/0280568 | A1 | 12/2005 | Rowland et al. | |
| 2008/0077327 | A1* | 3/2008 | Harris | B60R 9/04 701/301 |
| 2010/0245140 | A1 | 9/2010 | Iso et al. | |
| 2011/0316768 | A1* | 12/2011 | McRae | G06F 3/165 345/156 |

FOREIGN PATENT DOCUMENTS

| | | | | |
|---|---|---|---|---|
| DE | 10 2008 054789 | | 7/2010 | |
| DE | 102008054789 | * | 7/2010 | ............. G01S 13/93 |
| EP | 1 431 0622 | | 6/2004 | |
| WO | 2010/076061 | | 7/2010 | |

* cited by examiner

METHOD FOR AMPLIFYING AN ECHO SIGNAL SUITABLE FOR VEHICLE SURROUNDINGS DETECTION AND DEVICE FOR CARRYING OUT THE METHOD

FIELD OF THE INVENTION

The present invention relates to a method for amplifying an echo signal suitable for detection of a vehicle's surroundings and a device for carrying out the method. The present invention also relates to a vehicle assistance system having a device according to the present invention for amplifying an echo signal suitable for detection of a vehicle's surroundings.

BACKGROUND INFORMATION

A method for amplifying an echo signal suitable for detection of a vehicle's surroundings is discussed in publication DE 10 2008 054 789 A1, in which a gain factor is set as a function of a transit time of the echo signal. A variable amplifier is provided for this purpose, the gain curve optionally also having a sudden course in multiple steps. A complex operational amplifier circuit in which resistances are activated and deactivated for a sudden change in gain is shown as an exemplary embodiment. This also describes how the curve of the sudden change in gain must additionally be calibrated by a central signal processor.

The same publication describes how in systems, which sense the surroundings and carry out pulse-wise measurements, the evaluation complexity may be reduced with the aid of a transit time-dependent gain $V(\tau)$ since the signal strength becomes lower with an increase in echo transit time. This describes a continuous change in the input gain which may take place since the received signal is much less falsified by a continuous change in comparison with a sudden change.

In systems of an optimal configuration, it should be possible to vary the gain $V(\tau)$ in the range of $$1 \le \frac{V(\tau)}{V_0} < V_{max},$$

where $V_{max} > 100$ from the standpoint of the system.

FIGS. 1a and 1b show two possible curves of a desired transit time-dependent signal gain $V(\tau)$ as examples.

It is also believed to be understood from the related art how a transit time dependent gain may be implemented with little technical complexity by suitable wiring of an A/D converter, which may be in a recursive loop containing the signal reception, a certain part of the signal evaluation and optionally a suitable arrangement of generating a control signal for transit time-dependent gain regulation of an A/D converter in particular.

The recursive loop is not necessary for implementation of the transit time-dependent gain. If it is used, however, the transit time-dependent gain may be adapted to the prevailing signal situation, whereby the required dynamic range of the A/D converter may be reduced.

However, the technical implementation of amplifiers with a continuously adjustable gain is very difficult in particular because these amplifiers should also have a suitable dynamic range for the gain of incoming signals in addition to the adjustable gain range.

However, the implementation of N amplifiers having a fixed gain is implementable with very little effort. A very high gain $$V_{fixed\_total\_N} = \prod_{j=1}^{N} V_{fixed\ j}$$

may be implemented by a series circuit with such amplifiers and the signal is present partially amplified at the transitions between the amplifiers in each case:

$$V_{fixed\_total\ k} = \prod_{j=1}^{k} V_{fixed\ j}.$$

An equivalent situation applies for A/D converters. The range in which the reference voltage of A/D converters may be varied without any negative feedback effects on the quality of the A/D conversion is typically only in the range of 1 to 4.

There are therefore neither inexpensive A/D converters nor inexpensive variably adjustable amplifiers with which the required variable gain range $$1 \le \frac{V(\tau)}{V_0} < V_{max}$$

is implementable at approximately 50 kHz.

SUMMARY OF THE INVENTION

A method and a device according to the accompanying independent claims are made available.

With the method according to the present invention for amplifying an echo signal, an analog echo signal suitable for detection of a vehicle's surroundings is amplified with a gain which depends on the transit time of the echo signal. The analog echo signal is amplified with the aid of an amplifier having a plurality of outputs, each having a different, in particular fixed, gain and a downstream A/D converter having a time-variable reference voltage. The system is switched between different outputs of the amplifier at predefined switching points in time, and the reference voltage of the A/D converter is varied over time between the switching points in time, in such a way that the echo signal having a transit time-dependent total gain, which has a predefined characteristic, is present at the output of the A/D converter.

The device according to the present invention for a transit time-dependent gain of at least one echo signal, suitable for detection of a vehicle's surroundings, includes an amplifier having a plurality of outputs, each having a different gain, in particular a fixed gain, a downstream A/D converter having a time-variable reference voltage and a control device configured to switch between different outputs of the amplifier at predefined switching points in time and to generate a time-dependent total gain of the echo signal present at the output of the A/D converter and having a predefined characteristic with the aid of a suitable variation in the reference voltage of the A/D converter carried out between the switching points in time.

The further descriptions herein show refinements of the present invention.

Through a suitable variation of the reference voltage of the A/D converter between the switching points in time, a total gain of the echo signal, which is dependent on the transit time and has a desired characteristic, is generated from the partial gain of the echo signal generated by the amplifier between the switching points in time in a simple and economical manner.

Through suitable variation of the reference voltage of the A/D converter, the total dynamic range of the analog echo signal is easily imaged on a smaller effective total dynamic range, which results in a reduction in the computation effort required for evaluation of the echo signal.

The method according to the present invention also permits the use of an inexpensive A/D converter, whose reference voltage must be varied only in a small range.

In a particularly advantageous exemplary embodiment of the present invention, the analog echo signal is amplified with the aid of a series-connected chain of amplifiers of a fixed gain in particular and of the downstream A/D converter with the time-variable reference voltage.

The implementation of an amplifier by N series-connected amplifiers having a fixed gain is implementable at a very low cost and with low complexity in comparison with the implementation of an amplifier having a continuously adjustable gain. A very high gain $$V_{fixed\_total\_N} = \prod_{j=1}^{N} V_{fixed\ j}$$

is implementable by the series connection of amplifiers. A partially amplified signal having a partial gain of $$V_{fixed\_total\ k} = \prod_{j=1}^{k} V_{fixed\ j}$$

is present at the transitions between the amplifiers connected in series.

According to the present invention, the characteristic of the total gain is predefined in particular in pieces between the switching points in time.

Furthermore, according to the present invention, a method having a low level of complexity is made available for detection of a vehicle's surroundings with the aid of at least one echo signal in which at least one analog echo signal is amplified with the aid of a method according to the present invention, and at least the amplified echo signal for detection of a vehicle's surroundings is evaluated.

In addition, an inexpensive vehicle assistance system for detection of a vehicle's surroundings having a device according to the present invention for amplifying at least one echo signal suitable for detection of a vehicle's surroundings is made available according to the present invention, including an evaluation unit for detection of a vehicle's surroundings by at least one nonamplified echo signal and/or an echo signal amplified with the aid of the device according to the present invention.

Exemplary embodiments of the present invention are described in detail below with reference to the accompanying drawings.

DETAILED DESCRIPTION

Figure 1A:
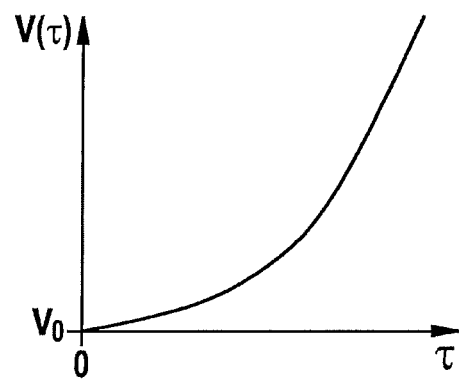
FIG. 1a shows one possible characteristic of a transit time-dependent signal gain according to the related art.
Figure 1B:
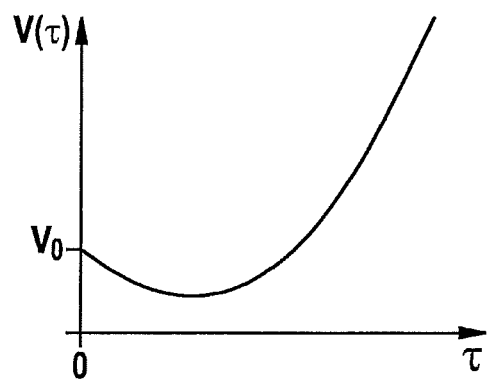
FIG. 1b show another possible characteristic of a transit time-dependent signal gain according to the related art.
Figure 2:
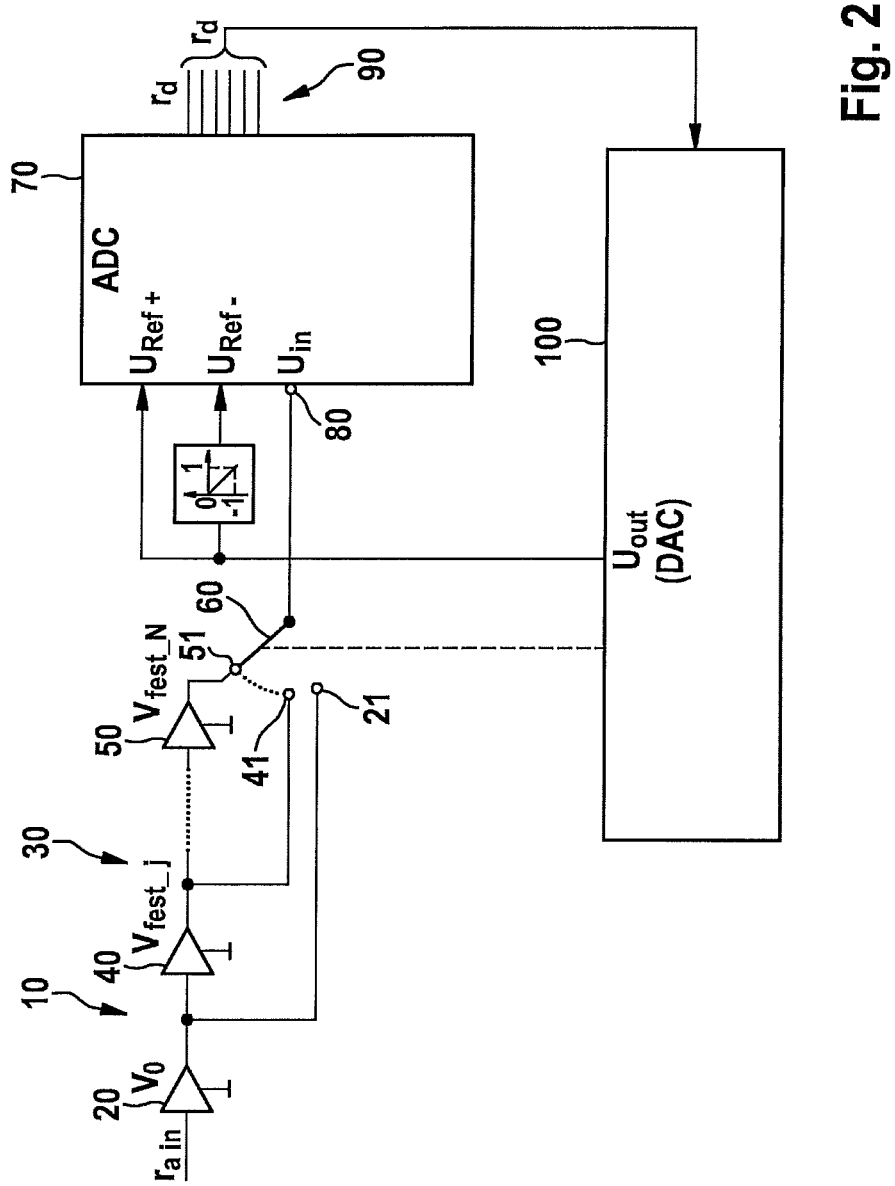
FIG. 2 shows a device according to the present invention for generating a transit time-dependent signal gain according to the first specific embodiment of the present invention.

FIG. 2 shows a device 10 according to the present invention for generating a transit time-dependent signal gain $V(\tau)$ according to the first specific embodiment of the present invention.

The analog input signal (echo signal) $r_{a\ in}$, which is dependent on transit time $\tau$ of the echo, having the usual center frequency of approximately 48 kHz in particular, has a basic gain $V_0$ with the aid of basic amplifier 20. A downstream amplifier 30 includes N series-connected, cascaded amplifiers 40, 50 having a fixed gain $V_{fixed\ j}$, which results in a fixed total input signal gain $$V_{fixed\_total\ N} = \prod_{j=1}^{N} V_{fixed\ j}.$$

FIG. 2 shows only two N series-connected amplifiers 40, 50.

A fixed gain $V_{fixed\_total\ k}$ is selected between switching points in time $\tau_k$, $\tau_{k+1}$ with the aid of at least one analog switch 60, and the analog signal amplified in this way is applied to a downstream A/D converter (ADC) 70. Control device 100 controls at least one analog switch 60 in such a way that N outputs 41, 51 of amplifier 30 are each connected in succession to input 80 of A/D converter at predefined switching points in time $\tau_1, \ldots, \tau_N$.

By varying the reference voltage of A/D converter $U_{Ref\ AD}(\tau)|_{\tau_k \leq \tau < \tau_{k+1}}$ with the aid of control device 100, a corresponding time-variant gain $V_{AD}(\tau)|_{\tau_k \leq \tau < \tau_{k+1}}$ is generated, in such a way that the total system gain of the scanned signals behaves according to a predefined characteristic $V(\tau)$. An output signal $r_d$ amplified by the total system gain is present at output 90 of A/D converter 70.

Figure 3:
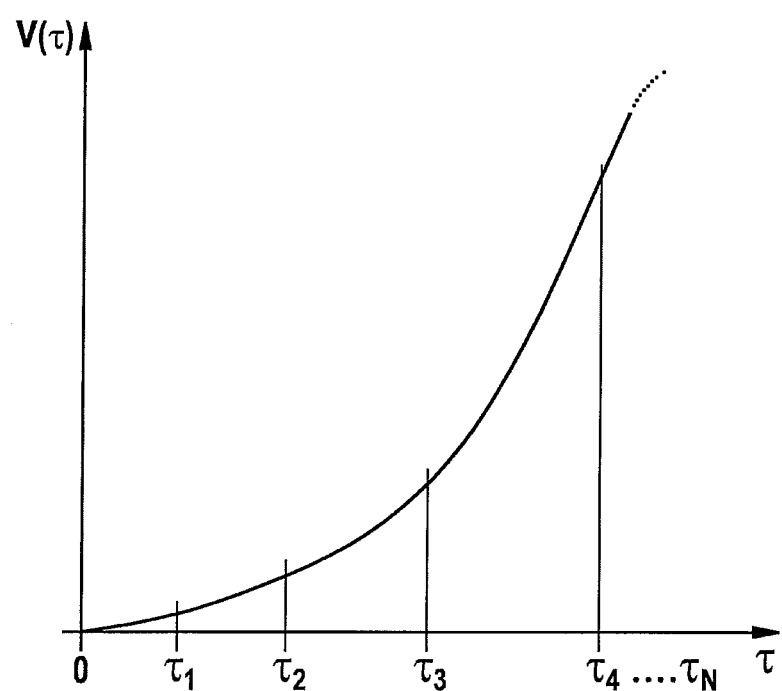
FIG. 3 shows a possible characteristic of the transit time-dependent signal gain according to the first specific embodiment of the present invention.

For the total system, the variation in reference voltage $U_{Ref\ AD}(\tau)|_{\tau_k \leq \tau < \tau_{k+1}}$ of A/D converter 70 acts like a time-variant gain $V_{AD}(\tau)|_{\tau_k \leq \tau < \tau_{k+1}}$ of the scanned signals. A desired gain characteristic $V(\tau)$ may be generated in pieces between switching points in time $0, \tau_1, \tau_2, \tau_3, \tau_4, \ldots, \tau_N$ as shown in FIG. 3.

In particular an inexpensive device 10 having an architecture with which the function of a desired, continuously adjustable gain is easily implementable in the required dynamic range $$1 \leq \frac{V(\tau)}{V_0} < V_{max}$$

is provided according to the present invention.

With the aid of device 10 according to the present invention for gain and subsequent analog/digital conversion of signals $r_{a\_in}$, a transit time-dependent gain $V(\tau)$ is implemented with the aid of a series-connected chain of amplifiers 40, 50 having a fixed gain $V_{fixed\_j}$ at which there is a switch between different effective fixed partial gains $V_{fixed\_total\_k}$ with the aid of at least one analog signal switch 60 at certain points in time $\tau_1, \tau_2, \ldots, \tau_N$, and downstream A/D conversion 70 is influenced with the aid of time-variable reference voltage $U_{Ref\_AD}(\tau)|_{\tau_k \leq \tau < \tau_{k+1}}$ between switching points in time $\tau_k, \tau_{k+1}$, in such a way that the total system gain is more or less equal to the desired transit time-dependent gain $V(\tau)$ due to this successive approximation.

In addition to the written disclosure above, reference is herewith made explicitly to the illustrations in FIGS. 2 and 3 for further disclosure of the present invention.

What is claimed is:

1. A method for amplifying an echo signal, the method comprising:
    amplifying an analog echo signal, which is for detecting a vehicle's surroundings, with a gain which depends on a transit time of the echo signal, wherein the analog echo signal is amplified with the aid of an amplifier unit having a plurality of outputs each having a different gain and a downstream A/D converter having a time-variable reference voltage, switching between different outputs of the amplifier unit at predefined switching points in time, wherein:
        the amplifier unit includes a series-connected chain of amplifiers,
        the analog echo signal is amplified with the aid of the series-connected chain of amplifiers having a fixed gain, and with the aid of the downstream A/D converter having the time-variable reference voltage, and
        each of the plurality of outputs of the amplifier unit is a respectively different output signal line branching from a different junction connecting different consecutive amplifiers in the series-connected chain of amplifiers, so that, except for an output signal line of a last amplifier in the series-connected chain of amplifiers, each of the different output signal lines bypasses every downstream amplifier in the series-connected chain of amplifiers; and
    varying the reference voltage of the A/D converter over time between the switching points in time so that the echo signal is available at the output of the A/D converter having a transit time-dependent total gain, which has a predefined characteristic.

2. The method of claim 1, wherein the characteristic is predefined in pieces between the switching points in time.

3. A method for detecting a vehicle's surroundings with the aid of at least one echo signal, the method comprising:
    amplifying at least one analog echo signal, by performing the following:
        amplifying an analog echo signal, which is suitable for detection of a vehicle's surroundings, with a gain which depends on a transit time of the echo signal, wherein the analog echo signal is amplified with the aid of an amplifier unit having a plurality of outputs each having a different gain and a downstream A/D converter having a time-variable reference voltage, switching between different outputs of the amplifier unit at predefined switching points in time, wherein:
            the amplifier unit includes a series-connected chain of amplifiers,
            the analog echo signal is amplified with the aid of the series-connected chain of amplifiers having a fixed gain, and with the aid of the downstream A/D converter having the time-variable reference voltage, and
            each of the plurality of outputs of the amplifier unit is a respectively different output signal line branching from a different junction connecting different consecutive amplifiers in the series-connected chain of amplifiers, so that, except for an output signal line of a last amplifier in the series-connected chain of amplifiers, each of the different output signal lines bypasses every downstream amplifier in the series-connected chain of amplifiers; and
        varying the reference voltage of the A/D converter over time between the switching points in time so that the echo signal is available at the output of the A/D converter having a transit time-dependent total gain, which has a predefined characteristic; and
    evaluating at least the amplified echo signal for detection of a vehicle's surroundings.

4. A device for amplifying at least one echo signal suitable for detecting a vehicle's surroundings, comprising:
    an amplifier unit to amplify an analog echo signal having a time-dependent gain, wherein the amplifier unit includes a plurality of outputs having different gains;
    a downstream A/D converter having a time-variable reference voltage; and
    a control device to switch between different outputs of the amplifier unit at predefined switching points in time, and to generate a time-dependent total gain of the echo signal, which is present at the output of the A/D converter and has a predefined characteristic by varying the reference voltage of the A/D converter between the switching points in time, wherein:
        the amplifier unit includes a series-connected chain of amplifiers,
        the analog echo signal is amplified with the aid of the series-connected chain of amplifiers having a fixed gain, and with the aid of the downstream A/D converter having the time-variable reference voltage, and
        each of the plurality of outputs of the amplifier unit is a respectively different output signal line branching from a different junction connecting different consecutive amplifiers in the series-connected chain of amplifiers, so that, except for an output signal line of a last amplifier in the series-connected chain of amplifiers, each of the different output signal lines bypasses every downstream amplifier in the series-connected chain of amplifiers.

5. The device of claim 4, wherein the control device is configured to connect at least one input of the A/D converter to multiple outputs, including all outputs of the amplifier in succession at predefined switching points in time with the aid of at least one analog switch.

6. The device of claim 4, wherein the characteristic is predefined in pieces between the switching points in time.

7. A vehicle assistance system for detecting a vehicle's surroundings, comprising:
    a device for amplifying at least one echo signal suitable for detecting a vehicle's surroundings, including:
        an amplifier unit to amplify an analog echo signal having a time-dependent gain, wherein the amplifier unit includes a plurality of outputs having different gains;

a downstream A/D converter having a time-variable reference voltage; and a control device to switch between different outputs of the amplifier unit at predefined switching points in time, and to generate a time-dependent total gain of the echo signal, which is present at the output of the A/D converter and has a predefined characteristic by varying the reference voltage of the A/D converter between the switching points in time;

an evaluation unit for detecting a vehicle's surroundings by at least one of (i) at least one echo signal amplified with the aid of the device, and (ii) a nonamplified echo signal, wherein:

the amplifier unit includes a series-connected chain of amplifiers, the analog echo signal is amplified with the aid of the series-connected chain of amplifiers having a fixed gain, and with the aid of the downstream A/D converter having the time-variable reference voltage, and each of the plurality of outputs of the amplifier unit is a respectively different output signal line branching from a different junction connecting different consecutive amplifiers in the series-connected chain of amplifiers, so that, except for an output signal line of a last amplifier in the series-connected chain of amplifiers, each of the different output signal lines bypasses every downstream amplifier in the series-connected chain of amplifiers.

* * * * *